United States Patent
Deihl

(10) Patent No.: US 6,767,925 B1
(45) Date of Patent: *Jul. 27, 2004

(54) SPRAYABLE ANALGESIC COMPOSITION AND METHOD OF USE

(76) Inventor: Joseph A. Deihl, 2401 S. 24th St., Phoenix, AZ (US) 85034

( * ) Notice: Subject to any disclaimer, the term of this patent is extended or adjusted under 35 U.S.C. 154(b) by 0 days.

This patent is subject to a terminal disclaimer.

(21) Appl. No.: 09/431,647

(22) Filed: Nov. 1, 1999

Related U.S. Application Data

(63) Continuation of application No. 08/739,654, filed on Oct. 31, 1996, now Pat. No. 5,981,591, which is a continuation of application No. 08/256,968, filed as application No. PCT/US92/10452 on Dec. 4, 1992, now abandoned.

(51) Int. Cl.$^7$ ............................................. A01N 37/10
(52) U.S. Cl. ...................... 514/568; 514/625; 514/629; 424/43; 564/192; 564/217; 564/218
(58) Field of Search ................................ 514/568, 625, 514/629; 424/43; 564/192, 217, 218

(56) References Cited

U.S. PATENT DOCUMENTS

| | | | |
|---|---|---|---|
| 3,644,626 A | | 2/1972 | Witzel et al. |
| 4,230,688 A | | 10/1980 | Rowsell et al. |
| 4,250,163 A | * | 2/1981 | Nagai et al. .................. 424/14 |
| 4,671,953 A | * | 6/1987 | Stanley et al. .............. 424/440 |
| 4,704,406 A | * | 11/1987 | Stanislaus et al. .......... 514/570 |
| 4,743,588 A | | 5/1988 | Mirejovsky et al. |
| 4,760,087 A | | 7/1988 | Zimmer et al. |
| 4,775,667 A | * | 10/1988 | Saitoh et al. ............... 514/160 |
| 4,861,797 A | | 8/1989 | Haas |
| 4,910,197 A | | 3/1990 | Beitner |
| 5,143,731 A | | 9/1992 | Viegas et al. |
| 5,331,000 A | | 7/1994 | Young et al. |
| 5,981,591 A | * | 11/1999 | Deihl ......................... 514/568 |

* cited by examiner

*Primary Examiner*—James H. Reamer
(74) *Attorney, Agent, or Firm*—Bryan Cave LLP

(57) ABSTRACT

A sprayable analgesic composition containing an analgesic which is absorbed into the bloodstream through the buccal mucosa and a pharmacologically acceptable liquid carrier.

14 Claims, No Drawings

SPRAYABLE ANALGESIC COMPOSITION AND METHOD OF USE

"This application is a continuation of application Ser. No. 08/739,654, filed Oct. 31, 1996, now U.S. Pat. No. 5,981,591 which is a continuation of application Ser. No. 08/256,968, filed Aug. 1, 1994, now abandoned which is the U.S. national stage of PCT/US92/10452 filed Dec. 4, 1992. The aforementioned applications are incorporated herein by reference".

This invention relates to sprayable analgesic compositions.

In another respect, the invention pertains to methods of administering analgesic compounds.

According to another aspect, the invention pertains to compositions and methods for oral administration of analgesic compounds by absorption through the buccal mucosa.

Topical application of analgesic compositions, i.e., by application to and absorption through the skin, is known. For example, the composition for topical application of a salicylate emulsion foot spray is disclosed in a patent to Modderno (U.S. Pat. No. 2,975,097).

BACKGROUND OF THE INVENTION

Sprayable topical analgesic anti-inflammatory compositions for treating skin rashes, etc. are disclosed in the Saitoh, et al. patent (U.S. Pat. No. 4,775,667).

Aerosol compositions for inhalation therapy, containing analgesics which are absorbed in the bronchioles and alveoli are disclosed in the patent to Porush, et al. (U.S. Pat. No. 2,868,691).

Liquid analgesics for oral administration are also known. For example, see the patent to Haas (U.S. Pat. No. 4,861,797) which discloses palatable liquid ibuprofen compositions.

To date, however, analgesic compounds have not been made available for administration by absorption through the buccal mucosa. It would be highly advantageous to provide such compositions in buccal absorption methods for administering analgesics, because such use and methods could be much more convenient for use by the general public, when it is not practical to use tabletted or swallowed liquid compositions. Moreover, compositions and methods for buccal mucosa administration of analgesics would be especially useful to persons who have impaired ability or aversion to swallowing tablets or liquid preparations.

Additionally, it would be advantageous to provide analgesic compositions and methods of administering analgesics which provide a desired physiological effect with the same or lower dosage compared to tabletted or liquid analgesic compositions.

SUMMARY OF THE INVENTION

I have now discovered liquid analgesic compositions and methods of administering analgesic compounds which are conveniently and inexpensively prepared, conveniently administered, and which may provide the desired physiological effect at a lower total dose than that obtained by use of prior tabletted or swallowed liquid compositions. My compositions and methods have been found particularly useful by persons who have a limited ability to use oral ingested tablets or liquids or have an aversion to such products. Further, it appears that a desired physiological result, i.e., alleviation of headaches can be obtained by administration of only approximately 1/20th of the dose normally recommended for tabletted analgesics such as acetaminophen.

DETAILED DESCRIPTION OF THE INVENTION

Briefly, in accordance with my invention, I provide a sprayable analgesic composition comprising an analgesic compound which is capable of introduction into the bloodstream by absorption through the buccal mucosa in a pharmacologically acceptable liquid carrier. The viscosity of the composition is adjusted to permit spray application of the composition to the buccal mucosa. In a preferred embodiment, the analgesic compound is acetaminophen. In another embodiment, the analgesic compound is ibuprofen. In the preferred embodiment, the liquid carrier is an aqueous ethanol liquid.

According to another embodiment of the invention, the above-described composition is contained in a measured dose spray dispenser which delivers a physiologically effective quantity of the composition in one or more, preferably in from 1–5, measured doses.

According to yet another embodiment of the invention, I provide a method of administering an analgesic compound to a subject comprising dispersing a quantity of an analgesic compound which is absorbed by the buccal mucosa in a pharmacologically acceptable liquid carrier to form a sprayable liquid composition, introducing the liquid composition into a measured dose spray dispenser, and applying a physiologically effective quantity of said composition by spraying from said dispenser on the buccal mucosa.

As used herein, the term analgesic is intended to describe any of the several known analgesics, such as acetaminophen, aspirin, ibuprofen, naproxen and the like, some of which also exhibit anti-inflammatory and/or anti-pyretic physiological activity.

The compositions preferably also include, in addition to the analgesic and liquid carrier components, other optional ingredients such as surfactants, humectants, preservatives, flavoring agents and other topical pharmaceutical adjuvants and excipients.

The compositions are prepared by art-recognized techniques which are typically used in the preparation of similar sprayable compositions.

EXAMPLES

Example I

The following example illustrates presently preferred practice of the invention and does not serve as a limitation on the scope of the invention which is limited only by the appended claims.

Having the following compositions:

| Component | Parts by Weight | Description |
| --- | --- | --- |
| SD alcohol | 50 | solvent |
| acetaminophen | 12 | analgesic |
| distilled water | 271 | carrier |
| sorbitol | .5 | surfactant |
| glycerine | 50 | humectant |
| Potassium carbonate | .7 | perservative |
| cyanocobalum | .02 | Vitamin $B_{12}$ |
| sucrose | 220 | flavor |
| pyridoxine | 3.6 | Vitamin $B_6$ |
| Polyoxyethylene sorbitan monooleate | 5 | surfactant |
| Toothpaste (Crest ®) | 3 | flavor |
| EDTA | .5 | preservative |
| fruit juice | 2.5 | flavor |

The above-described composition is packaged in a measured dose spray dispenser containing enough of the composition to provide 240 spray doses containing 1 milligram acetaminophen per spray. (One spray equals 50 microliters.)

Example II

Patients with common headaches are instructed to use the spray dispensers by administering two of the measured dose sprays into the mouth, on the inner cheeks and under the tongue, wait five minutes and then administer two more sprays in the same manner.

Simple headaches are relieved with one or two repetitions of the above procedure.

Example III

Procedures of Examples I and II are repeated, except that the acetaminophen is replaced with ibuprofen. Similar results are obtained.

The sprayable compositions are, desirably, solutions of the active ingredients and other components. However, it is also contemplated that stable suspensions of the active ingredient and other components can be employed.

Having described my invention in such terms as to enable those skilled in the art to understand and practice it and having identified and disclosed presently preferred embodiments thereof, I claim:

1. A sprayable dosage for direct sprayable application to the buccal mucosa of the mouth of a user, said dosage comprising:
   (a) a pharmacologically acceptable liquid carrier;
   (b) a physiologically effective amount of an analgesic compound carried by said pharmacologically acceptable liquid carrier, wherein said analgesic compound is selected from the group consisting of acetominophen, aspirin, ibuprofen and naproxen; and
   (c) one or more surfactants;
   (d) wherein direct absorption of said physiologically effective amount of analgesic compound into the bloodstream occurs through the surface of the buccal mucosa of the mouth upon direct application of said sprayable dosage to the surface of the buccal mucosa of the mouth; and
   (e) a target site of analgesic action is other than the buccal cavity or buccal sub-mucosal tissue.

2. A sprayable dosage according to claim 1, wherein the pharmacologically acceptable liquid carrier is an aqueous ethanol liquid.

3. A sprayable dosage according to claim 1, further comprising one or more ingredients selected from the group consisting of pharmacologically acceptable surfactants, humectants, preservatives, flavoring agents and vitamins.

4. A sprayable dosage according to claim 2, wherein the analgesic compound is ibuprofen and the liquid carrier is an ethanol liquid.

5. A sprayable dosage according to claim 2, wherein the analgesic compound is acetaminophen and the liquid carrier is an ethanol liquid.

6. A sprayable dosage for direct sprayable application of said dosage to the buccal mucosa of the mouth of a user, said dosage comprising a solvent, an analgesic, a carrier, surfacant, humectant, preservative and flavor.

7. A sprayable dosage according to claim 6, further comprising one or more vitamins.

8. A sprayable dosage according to claim 6 comprising SD alcohol, acetaminophen, water, sorbitol glycerine, potassium sorbate, cyanocobalum, sucrose, pyridoxine, polyoxyethylene sorbitan monooleate, EDTA, and fruit juice.

9. A method for administering an analgesic comprising spraying a sprayable dosage for direct sprayable application to the buccal mucosa of the mouth of a user, said dosage comprising:
   (a) a pharmacologically acceptable liquid carrier;
   (b) a physiologically effective amount of an analgesic compound carried by said pharmacologically acceptable liquid carrier, wherein said analgesic compound is selected from the group consisting of acetominophen, aspirin, ibuprofen and naproxen; and
   (c) one or more surfactants;
   (d) wherein direct absorption of said physiologically effective amount of analgesic compound into the bloodstream occurs through the surface of the buccal mucosa of the mouth upon direct application of said sprayable dosage to the surface of the buccal mucosa of the mouth, into the mouth of a subject in at least one measured dose; and
   (e) a target site of analgesic action is other than the buccal cavity or the buccal sub-mucosal tissue.

10. A method according to claim 9 comprising spraying the dosage in 1, 2, 3, 4 or 5 measured doses.

11. A method for relieving a headache comprising spraying a sprayable dosage for direct sprayable application to the buccal mucosa of the mouth of a user, said dosage comprising:
   (a) a pharmacologically acceptable liquid carrier;
   (b) a physiologically effective amount of an analgesic compound carried by said pharmacologically acceptable liquid carrier, wherein said analgesic compound is selected from the group consisting of acetominophen, aspirin, ibuprofen and naproxen; and
   (c) one or more surfactants;
   (d) wherein direct absorption of said physiologically effective amount of analgesic compound into the bloodstream occurs through the surface of the buccal mucosa of the mouth upon direct application of said sprayable dosage, into the mouth of a subject having a headache in at least of measured dose; and,
   (e) a target site of analgesic action other than the buccal cavity or the buccal sub-mucosal tissue.

12. A method according to claim 11 comprising spraying the dosage in 1, 2, 3, 4, or 5 measured doses.

13. A sprayable dosage according to claim 1 in the form of a solution.

14. A sprayable dosage according to claim 1 in the form of a stable suspension.

* * * * *